US011399707B2

United States Patent
Yoshioka et al.

(10) Patent No.: US 11,399,707 B2
(45) Date of Patent: Aug. 2, 2022

(54) ENDOSCOPE APPARATUS

(71) Applicant: FUJIFILM Corporation, Tokyo (JP)

(72) Inventors: Masato Yoshioka, Kanagawa (JP); Takeichi Tatsuta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 334 days.

(21) Appl. No.: 16/459,595

(22) Filed: Jul. 1, 2019

(65) Prior Publication Data

US 2020/0008661 A1 Jan. 9, 2020

(30) Foreign Application Priority Data

Jul. 4, 2018 (JP) .............................. JP2018-127445

(51) Int. Cl.
| | | |
|---|---|---|
| *A61B 1/06* | (2006.01) | |
| *A61B 1/04* | (2006.01) | |
| *G02B 23/24* | (2006.01) | |
| *A61B 1/00* | (2006.01) | |

(52) U.S. Cl.
CPC .............. *A61B 1/0676* (2013.01); *A61B 1/04* (2013.01); *A61B 1/0623* (2013.01); *A61B 1/0638* (2013.01); *G02B 23/2461* (2013.01); *A61B 1/00009* (2013.01); *A61B 1/00045* (2013.01)

(58) Field of Classification Search
CPC ....... A61B 1/00009; A61B 1/04; A61B 1/041; A61B 1/05; A61B 1/06; A61B 1/0623; A61B 1/0661; A61B 1/0676; A61B 1/0684; A61B 5/107; A61B 5/1072; A61B 5/1076; A61B 5/1079; G02B 23/2461; H04N 2005/2256; H04N 13/207
See application file for complete search history.

(56) References Cited

U.S. PATENT DOCUMENTS

| | | | |
|---|---|---|---|
| 4,980,763 A | 12/1990 | Lia | |
| 5,436,655 A | 7/1995 | Hiyama et al. | |
| 9,261,356 B2 * | 2/2016 | Lampert | ............... A61C 9/0053 |
| 9,545,220 B2 * | 1/2017 | Sidlesky | ................... G06T 7/70 |
| 2015/0215614 A1 | 7/2015 | Witt | |

(Continued)

FOREIGN PATENT DOCUMENTS

| | | | | |
|---|---|---|---|---|
| CN | 110418596 A | * | 11/2019 | ............. A61B 1/045 |
| JP | H0313805 | | 1/1991 | |
| JP | H03231622 | | 10/1991 | |

(Continued)

OTHER PUBLICATIONS

"Office Action of Japan Counterpart Application", dated Apr. 13, 2021, with English translation thereof, pp. 1-12.

(Continued)

*Primary Examiner* — Michael J Carey
*Assistant Examiner* — Julianna J Nicolaus
(74) *Attorney, Agent, or Firm* — JCIPRNET

(57) ABSTRACT

An auxiliary measurement light-emitting unit emits auxiliary measurement light that is planar light including at least two first feature lines. A taken image obtained through the imaging of a subject includes an intersection curve and at least two first spots that are formed at positions corresponding to first feature lines on the intersection curve. Measurement information representing the actual size of the subject is displayed in the taken image by using the positions of the first spots.

13 Claims, 13 Drawing Sheets

(56) References Cited

U.S. PATENT DOCUMENTS

2017/0172382 A1    6/2017  Nir et al.
2019/0306467 A1   10/2019  Sonoda et al.

FOREIGN PATENT DOCUMENTS

| | | | |
|---|---|---|---|
| JP | H07136101 | 5/1995 | |
| JP | H07136101 A * | 5/1995 | |
| JP | 2005279028 | 10/2005 | |
| JP | 2005279028 A * | 10/2005 | |
| JP | 2011234871 | 11/2011 | |
| JP | 2012147857 | 8/2012 | |
| JP | 2012147857 A * | 8/2012 | |
| JP | 2013005830 | 1/2013 | |
| JP | 2015531271 | 11/2015 | |
| JP | 6810711 B2 * | 6/2016 | ........... A61B 5/6844 |
| JP | 2017508529 | 3/2017 | |
| JP | 6810711 B2 * | 1/2021 | ........... G06T 7/0008 |
| WO | 2015132778 | 9/2015 | |
| WO | 2018159292 | 9/2018 | |
| WO | 2018230099 | 12/2018 | |

OTHER PUBLICATIONS

"Search Report of Europe Counterpart Application", dated Nov. 21, 2019, p. 1-p. 7.
"Office Action of Japan Counterpart Application" with English translation thereof, dated Jul. 6, 2021, p. 1-p. 12.
Office Action of European Counterpart Application, dated Oct. 12, 2021, pp. 1-4.

* cited by examiner

ENDOSCOPE APPARATUS

CROSS-REFERENCE TO RELATED APPLICATIONS

This application claims priority under 35 U.S.C § 119(a) to Japanese Patent Application No. 2018-127445 filed on Jul. 4, 2018. The above application is hereby expressly incorporated by reference, in its entirety, into the present application.

BACKGROUND OF THE INVENTION

1. Field of the Invention

The present invention relates to an endoscope apparatus that measures the size of a subject.

2. Description of the Related Art

A distance to an object to be observed, the size of an object to be observed, or the like is acquired in an endoscope apparatus. For example, in JP1991-231622A (JP-H03-231622A), a beam is applied to a subject from the distal end portion of an endoscope and a distance to an object to be observed and the like are calculated from the position and angle of a point of the beam that is formed on the subject by the application of the beam. Further, in JP2017-508529A (corresponding to US2016/287141A1), planar light is applied to a subject to form an intersection curve where the planar light and the subject cross each other on the subject and a distance between two points on the intersection curve is calculated. Furthermore, in JP2013-005830A, in a case where two illumination windows emitting illumination light are provided at the distal end portion of an endoscope, two bright spots are formed on a subject by two pieces of illumination light emitted from these two illumination windows and a distance to an object to be observed is calculated from a distance between the two bright spots.

SUMMARY OF THE INVENTION

Since subjects to be observed by an endoscope in a medical field often have a three-dimensional shape, there is a need for a method of acquiring measurement information suitable for a three-dimensional shape. In this regard, since only positional information about one point based on a beam is obtained in the JP1991-231622A (JP-H03-231622A), a method disclosed in JP1991-231622A (JP-H03-231622A) is not suitable for the acquisition of measurement information in a case where a subject has a three-dimensional shape.

On the other hand, since a distance is calculated from two points on the intersection curve in JP2017-508529A, a method disclosed in JP2017-508529A is suitable for the acquisition of measurement information in a case where a subject has a three-dimensional shape. However, since a user needs to designate two points on the intersection curve by a graphical user interface (GUI), the method disclosed in JP2017-508529A is inconvenient in the operation of an endoscope where a user uses both hands. Further, since the intersection curve is always changed, the intersection curve is designated in a static image in JP2017-508529A. For this reason, there is a need for a method for measuring a distance between two points not in a static image but in a motion picture.

Further, in JP2013-005830A, measurement information in a case where a subject has a three-dimensional shape can be more accurately acquired using positional information about a portion between two bright spots. However, since only positional information about two bright spots is obtained in the case of JP2013-005830A, it is difficult to grasp information about a portion between these two bright spots, for example, the undulation of a subject and the like.

An object of the invention is to provide an endoscope apparatus that can simply and accurately obtain measurement information without imposing a burden on a user in a case where a subject has a three-dimensional shape.

An endoscope apparatus according to an aspect of the invention comprises an auxiliary measurement light-emitting unit that emits auxiliary measurement light as planar light including at least two first feature lines, an imaging element that images a subject illuminated with the auxiliary measurement light, an image acquisition unit that acquires a taken image obtained in a case where the subject is imaged by the imaging element, the taken image including an intersection curve formed on the subject and at least two first feature points formed at positions corresponding to the first feature lines on the intersection curve, a position specifying unit that specifies at least positions of the first feature points on the basis of the taken image, and a display control unit that displays measurement information representing an actual size of the subject in the taken image by using the positions of the first feature points.

It is preferable that the measurement information includes a first straight-line distance between the two first feature points. It is preferable that the measurement information includes a second straight-line distance between one of the two first feature points and a specific point other than the two first feature points. It is preferable that the measurement information includes a length of a specific intersection curved portion of the intersection curve positioned between the two first feature points, the position specifying unit specifies a position of the specific intersection curved portion, and the display control unit displays the length of the specific intersection curved portion in the taken image by using the positions of the first feature points and the position of the specific intersection curved portion.

It is preferable that the auxiliary measurement light includes a plurality of second feature lines, which are different from the first feature lines, between the two first feature lines, the specific intersection curved portion includes a plurality of second feature points formed on the intersection curve by the second feature lines so as to be smaller than the first feature points, and the position specifying unit specifies the position of the specific intersection curved portion from the plurality of second feature points included in the taken image.

It is preferable that the endoscope apparatus further comprises a measurement information switching unit that switches the measurement information to be displayed in the taken image to any one of a plurality of pieces of measurement information or a combination of two or more of a plurality of pieces of measurement information in a case where there are a plurality of pieces of measurement information. It is preferable that the endoscope apparatus further comprises a static image-acquisition command unit giving a static image-acquisition command to acquire a static image of the taken image and the measurement information is also stored together in a case where the static image-acquisition command is given.

It is preferable that the endoscope apparatus further comprises a first light source unit emitting illumination light for illuminating the subject and the auxiliary measurement light-emitting unit includes a second light source unit provided independently of the first light source unit and an auxiliary measurement optical element used to obtain the auxiliary measurement light from light emitted from the second light source unit. It is preferable that the auxiliary measurement light-emitting unit includes a specific optical member used to emit the auxiliary measurement light toward the subject in a state where an optical axis of the imaging element and an optical axis of the auxiliary measurement light cross each other. It is preferable that the specific optical member is provided with an anti-reflection portion. It is preferable that the auxiliary measurement light-emitting unit includes an auxiliary measurement slit used to emit the auxiliary measurement light toward the subject in a state where an optical axis of the imaging element and an optical axis of the auxiliary measurement light cross each other. It is preferable that the second light source unit is a laser light source. It is preferable that a wavelength of light emitted from the second light source unit is in the range of 495 nm to 570 nm.

According to the aspect of the invention, it is possible to simply and accurately obtain measurement information without imposing a burden on a user in a case where a subject has a three-dimensional shape.

DESCRIPTION OF THE PREFERRED EMBODIMENTS

Figure 1:
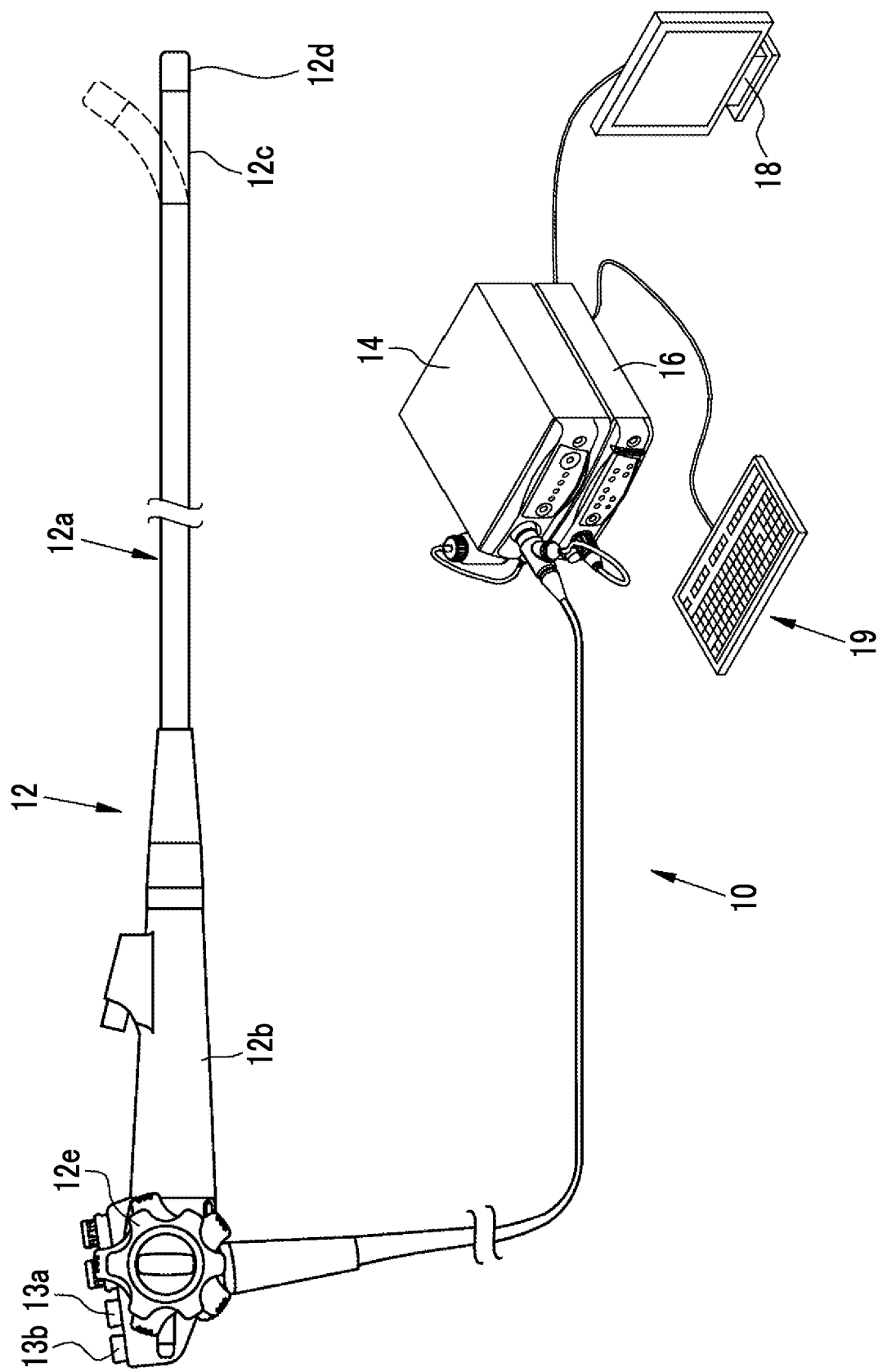
FIG. 1 is a diagram showing the appearance of an endoscope apparatus.

As shown in FIG. 1, an endoscope apparatus 10 includes an endoscope 12, a light source device 14, a processor device 16, a monitor 18, and a user interface 19. The endoscope 12 is optically connected to the light source device 14, and is electrically connected to the processor device 16. The processor device 16 is electrically connected to the monitor 18 (display unit) that displays an image. The user interface 19 is connected to the processor device 16, and is used for various setting operations and the like for the processor device 16. The user interface 19 includes a mouse and the like in addition to a keyboard shown in FIG. 1.

The endoscope 12 includes an insertion part 12a that is to be inserted into a subject, an operation part 12b that is provided at a proximal end portion of the insertion part 12a, and a bendable portion 12c and a distal end portion 12d that are provided at a distal end of the insertion part 12a. The bendable portion 12c operates to be bent by the operation of an angle knob 12e of the operation part 12b. The distal end portion 12d is oriented in a desired direction by the bending operation of the bendable portion 12c.

The endoscope 12 has a normal mode and a length measurement mode, and these two modes are switched by a mode changeover switch 13a (mode switching unit) that is provided on the operation part 12b of the endoscope 12. The normal mode is a mode where an object to be observed is illuminated with illumination light. In the length measurement mode, an object to be observed is illuminated with illumination light or auxiliary measurement light and measurement information used to measure the size and the like of the object to be observed is displayed in a taken image obtained through the imaging of the object to be observed. The measurement information of this embodiment represents the actual size of a subject.

Further, the operation part 12b of the endoscope 12 is provided with a freeze switch 13b (static image-acquisition command unit) that is used to give a static image-acquisition command to acquire the static image of a taken image. In a case where a user operates the freeze switch 13b, the screen of the monitor 18 is frozen and displayed and an alert sound (for example, "beep") informing the acquisition of a static image is generated together. Then, the static images of the taken image, which are obtained before and after the operation timing of the freeze switch 13b, are stored in a static image storage unit 37 (see FIG. 3) provided in the processor device 16. Furthermore, it is preferable that measurement information to be described later is also stored together with the static image of the taken image in a case where the endoscope 12 is set to the length measurement mode. The static image storage unit 37 is a storage unit, such as a hard disk or a universal serial bus (USB) memory. In a case where the processor device 16 can be connected to a network, the static image of the taken image may be stored in a static image storage server (not shown), which is connected to a network, instead of or in addition to the static image storage unit 37.

A static image-acquisition command may be given using an operation device other than the freeze switch 13b. For example, a foot pedal may be connected to the processor device 16, and a static image-acquisition command may be given in a case where a user operates the foot pedal (not shown) with a foot. A static image-acquisition command may be given by a foot pedal that is used to switch a mode. Further, a gesture recognition unit (not shown), which recognizes the gestures of a user, may be connected to the processor device 16, and a static image-acquisition command may be given in a case where the gesture recognition unit recognizes a specific gesture of a user. The gesture recognition unit may also be used to switch a mode.

Furthermore, a visual line input unit (not shown), which is provided close to the monitor 18, may be connected to the processor device 16, and a static image-acquisition command may be given in a case where the visual line input unit recognizes that a user's visual line is in a predetermined area of the monitor 18 for a predetermined time or longer. Further, a voice recognition unit (not shown) may be connected to the processor device 16, and a static image-acquisition command may be given in a case where the voice recognition unit recognizes a specific voice generated by a user. The voice recognition unit may also be used to switch a mode. Furthermore, an operation panel (not shown), such as a touch panel, may be connected to the processor device 16, and a static image-acquisition command may be given in a case where a user makes a specific operation on the operation panel. The operation panel may also be used to switch a mode.

Figure 2:
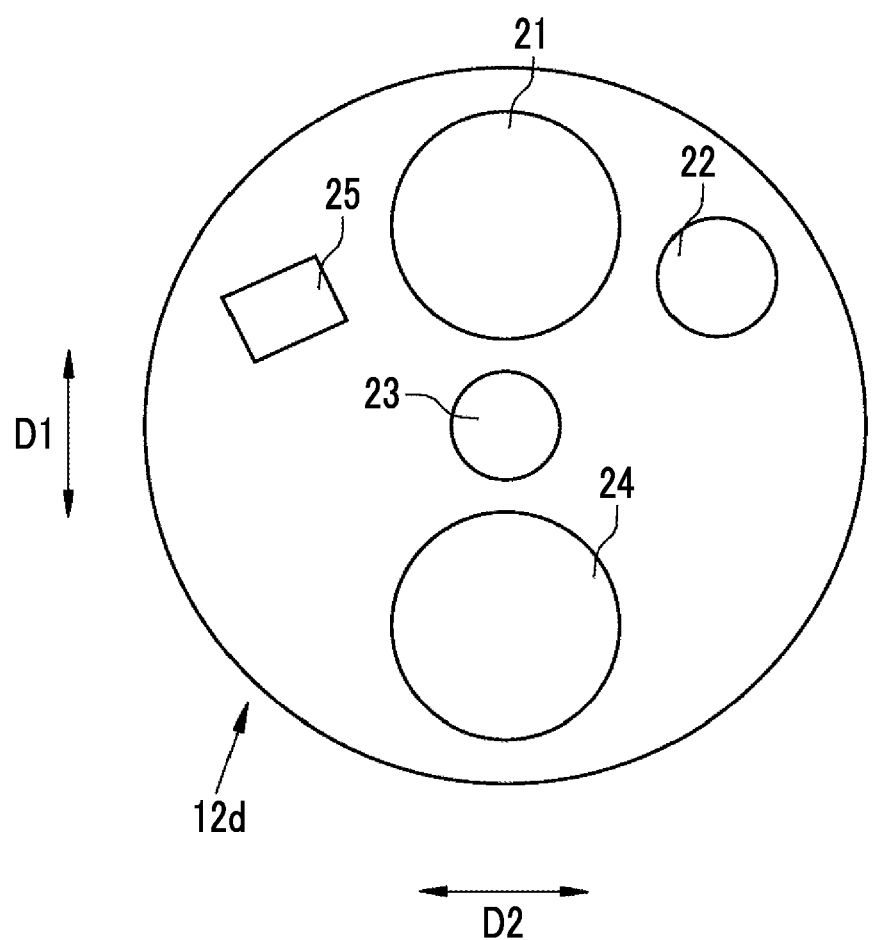
FIG. 2 is a plan view of a distal end portion of an endoscope.

As shown in FIG. 2, the distal end portion of the endoscope 12 has a substantially circular shape; and is provided with an objective lens 21 that is positioned closest to a subject among optical members of an imaging optical system of the endoscope 12, an illumination lens 22 that is used to irradiate the subject with illumination light, an auxiliary measurement optical element 23 that is used to illuminate the subject with auxiliary measurement light to be described later, an opening 24 that allows a treatment tool to protrude toward the subject, and an air/water supply nozzle 25 that is used to supply air and water.

An optical axis Ax of the objective lens 21 extends in a direction perpendicular to the plane of paper. A vertical first direction D1 is orthogonal to the optical axis Ax, and a horizontal second direction D2 is orthogonal to the optical axis Ax and the first direction D1. The objective lens 21 and the auxiliary measurement optical element 23 are arranged in the first direction D1.

Figure 3:
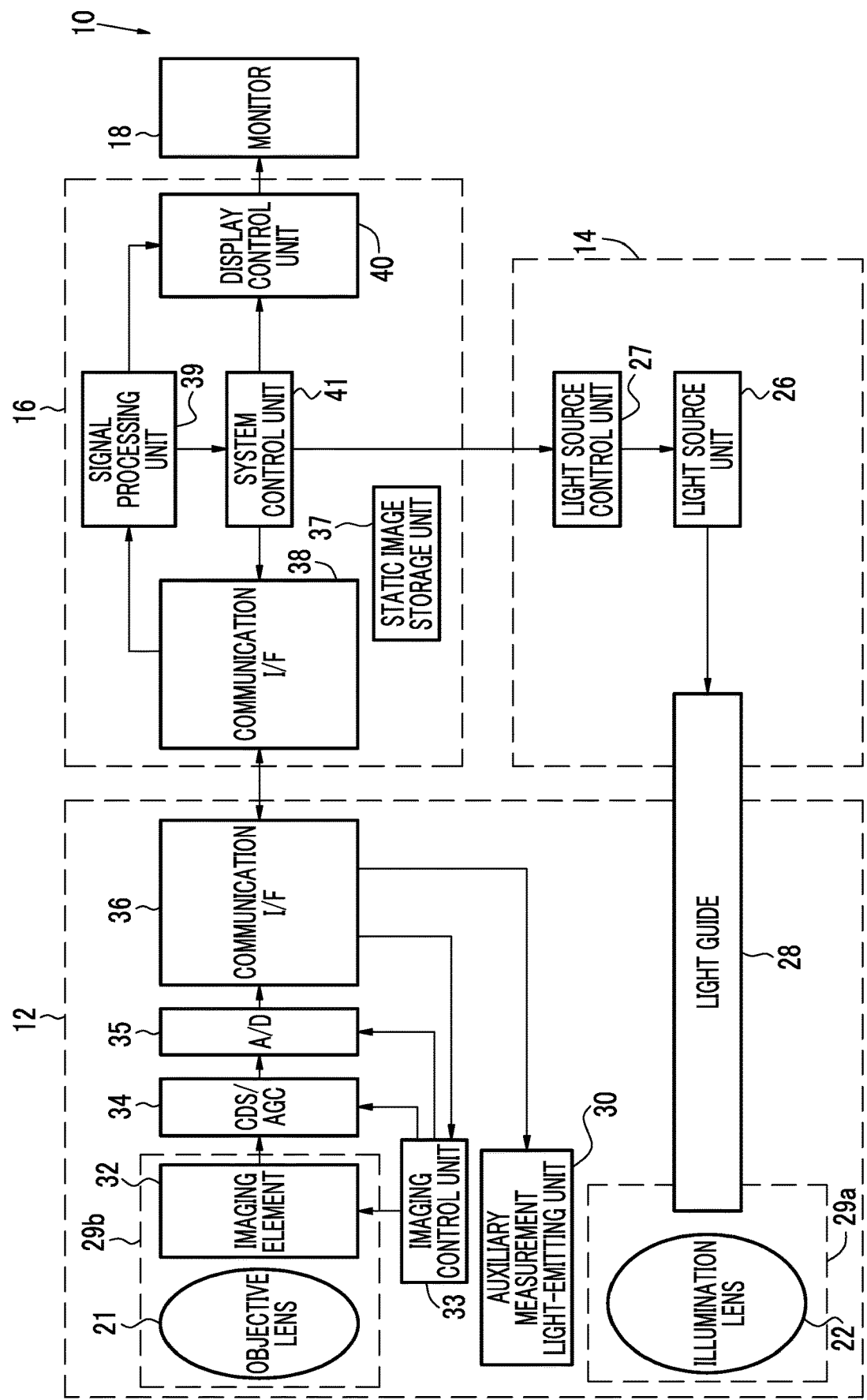
FIG. 3 is a block diagram showing the function of the endoscope apparatus.

As shown in FIG. 3, the light source device 14 comprises a light source unit 26 (first light source unit) and a light source control unit 27. The light source unit 26 generates illumination light that is used to illuminate the subject. Illumination light emitted from the light source unit 26 is incident on a light guide 28, and is applied to the subject through the illumination lens 22. In the light source unit 26, a white light source emitting white light, a plurality of light sources, which includes a white light source and a light source emitting another color light (for example, a blue light source emitting blue light), or the like is used as a light source of illumination light. The light source control unit 27 is connected to a system control unit 41 of the processor device 16. The light source control unit 27 controls the light source unit on the basis of a command output from the system control unit 41. In a case where the endoscope 12 is set to the normal mode, the light source control unit 27 controls the light source unit so that the light source unit emits illumination light. In a case where the endoscope 12 is set to the length measurement mode, the light source control unit 27 controls the light source unit so that the light source unit emits illumination light and auxiliary measurement light. Special light, which has a wavelength in a blue wavelength range between a blue wavelength range and a red wavelength range and has high intensity, may be used other than white light as the illumination light.

The distal end portion 12d of the endoscope 12 is provided with an illumination optical system 29a, an imaging optical system 29b, and an auxiliary measurement light-emitting unit 30. The illumination optical system 29a includes the illumination lens 22, and an object to be observed is irradiated with light, which is emitted from the light guide 28, through the illumination lens 22. The imaging optical system 29b includes the objective lens 21 and an imaging element 32. Light reflected from the object to be observed is incident on the imaging element 32 through the objective lens 21. Accordingly, the reflected image of the object to be observed is formed on the imaging element 32.

The imaging element 32 is a color imaging sensor, and takes the reflected image of the subject and outputs image signals. It is preferable that the imaging element 32 is a charge coupled device (CCD) imaging sensor, a complementary metal-oxide semiconductor (CMOS) imaging sensor, or the like. The imaging element 32 used in the invention is a color imaging sensor that is used to obtain RGB image signals corresponding to three colors of R (red), G (green), and B (blue). The imaging element 32 is controlled by an imaging control unit 33.

The image signals output from the imaging element 32 are transmitted to a CDS/AGC circuit 34. The CDS/AGC circuit 34 performs correlated double sampling (CDS) or auto gain control (AGC) on the image signals that are analog signals. The image signals, which have been transmitted through the CDS/AGC circuit 34, are converted into digital image signals by an analog/digital converter (A/D converter) 35. The digital image signals, which have been subjected to A/D conversion, are input to the processor device 16 through a communication interface (I/F) 36.

The processor device 16 comprises a communication interface (I/F) 38 that is connected to the communication I/F of the endoscope 12, a signal processing unit 39, a display control unit 40, and a system control unit 41. The communication I/F receives the image signals, which are transmitted from the communication I/F 36 of the endoscope 12, and transmits the image signals to the signal processing unit 39. A memory, which temporarily stores the image signals received from the communication I/F 38, is built in the signal processing unit 39, and the signal processing unit 39 processes an image signal group, which is a set of the image signals stored in the memory, to generate the taken image. In a case where the endoscope 12 is set to the length measurement mode, the signal processing unit 39 may be adapted to perform structure-enhancement processing for enhancing structures, such as blood vessels, or color difference-enhancement processing for increasing a color difference between a normal area and a specific area, such as a lesion area, of the object to be observed on the taken image.

The display control unit 40 displays the taken image, which is generated by the signal processing unit 39, on the monitor 18. The system control unit 41 controls the imaging element 32 through the imaging control unit 33 that is provided in the endoscope 12. The imaging control unit 33 also controls the CDS/AGC circuit 34 and the A/D converter 35 according to the control of the imaging element 32. Further, the system control unit 41 controls the light source unit 26 through the light source control unit 27. Furthermore, the system control unit 41 controls a light source 30a (see FIG. 4) of the auxiliary measurement light-emitting unit 30.

Figure 4:
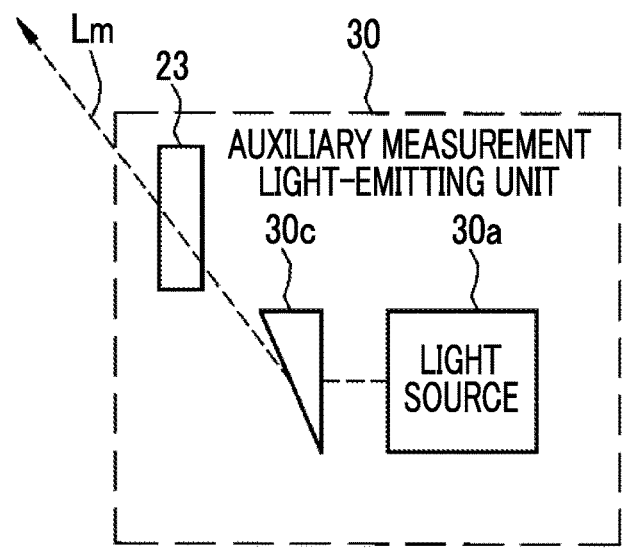
FIG. 4 is a block diagram of an auxiliary measurement light-emitting unit.

As shown in FIG. 4, the auxiliary measurement light-emitting unit 30 comprises a light source 30a, a prism 30c, and the auxiliary measurement optical element 23. The light source 30a (second light source unit) is to emit light having a color that can be detected by pixels of the imaging element 32 (specifically visible light), and includes a light-emitting element, such as a laser diode (LD) or a light-emitting diode (LED), and a condenser lens that condenses light emitted from the light-emitting element.

The wavelength of light emitted from the light source 30a is in the range of, for example, 495 nm to 570 nm, but is not limited thereto. Since green light having a wavelength in the range of 495 nm to 570 nm is used, a position specifying unit 50 easily recognizes the positions of first spots SP1 or second spots SP2 to be described later even though the subject is illuminated with special light. A wavelength in the range of 600 nm to 650 nm may be used as another wavelength. The light source 30a is controlled by the system control unit 41, and emits light on the basis of a command output from the system control unit 41.

The prism 30c (specific optical member) is an optical member that is used to change the travel direction of light emitted from the light source 30a. The prism 30c changes the travel direction of the light emitted from the light source 30a so that the light emitted from the light source 30a crosses the visual field of the imaging optical system including the objective lens 21 and lens groups. The subject is irradiated with light, which is emitted from the prism 30c, through the auxiliary measurement optical element 23. Further, it is preferable that an anti-reflection (AR) coating (anti-reflection portion) is provided on the prism 30c. The reason why the anti-reflection coating is performed as described above is that it is difficult for a position specifying unit 50 to be described later to recognize the positions of first spots SP1 or second spots SP2 to be formed on the subject by auxiliary measurement light in a case where auxiliary measurement light is reflected without being transmitted through the prism 30c and a ratio of auxiliary measurement light to be applied to the subject is reduced.

The auxiliary measurement optical element 23 is formed of a diffractive optical element (DOE) and converts light, which is emitted from the prism 30c, into auxiliary measurement light that is used to obtain measurement information. The details of the auxiliary measurement light and the travel direction of the auxiliary measurement light will be described later.

The auxiliary measurement light-emitting unit 30 has only to be capable of emitting auxiliary measurement light toward the visual field of the imaging optical system. For example, the light source 30a may be provided in the light source device and light emitted from the light source 30a may be guided to the auxiliary measurement optical element 23 by optical fibers. Further, the prism 30c may not be used and the directions of the light source 30a and the auxiliary measurement optical element 23 may be inclined with respect to the optical axis Ax so that auxiliary measurement light is emitted in a direction crossing the visual field of the imaging optical system. In this case, an auxiliary measurement slit is fainted at the distal end portion 12d of the endoscope so that the auxiliary measurement light is emitted.

Figure 5:
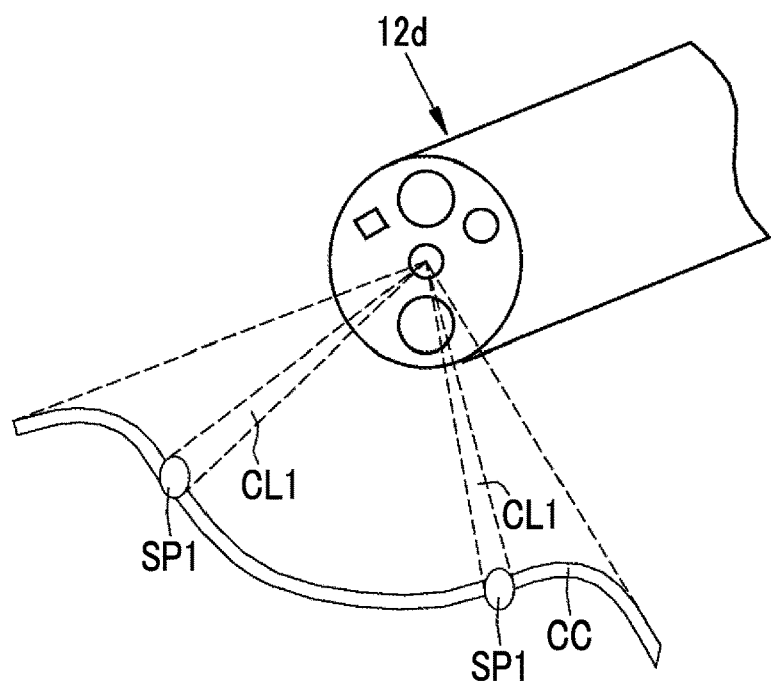
FIG. 5 is a diagram illustrating auxiliary measurement light that is emitted from the distal end portion of the endoscope and reaches a subject and includes two first feature lines.
Figure 6:
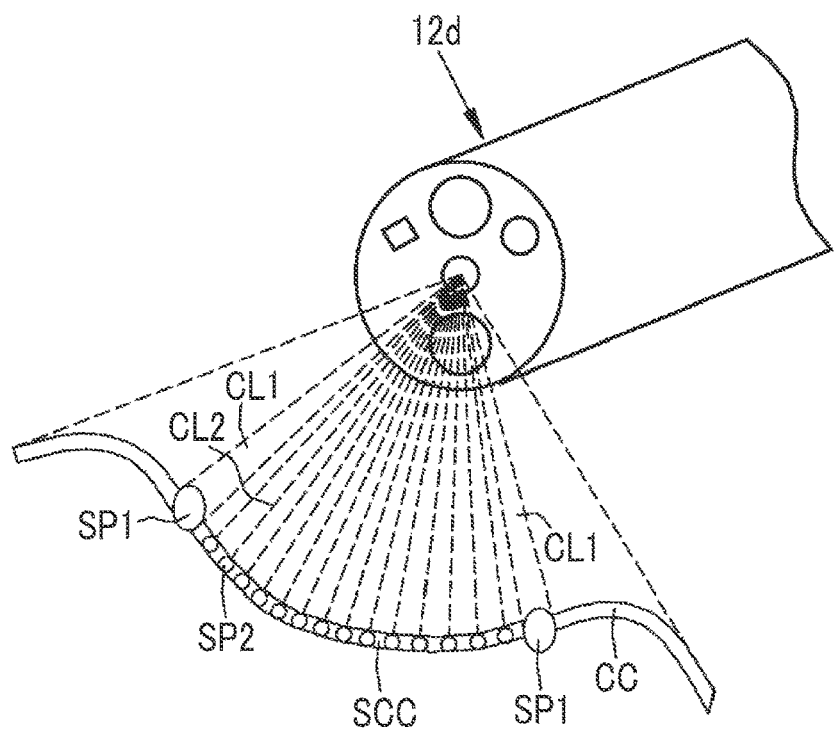
FIG. 6 is a diagram illustrating auxiliary measurement light that is emitted from the distal end portion of the endoscope and reaches a subject and includes two first feature lines and a plurality of second feature lines.

As shown in FIG. 5, the auxiliary measurement light is formed of planar light including at least two first feature lines CL. In a case where the subject is irradiated with the auxiliary measurement light, an intersection curve CC is formed according to undulations on the subject and first spots SP1 (first feature points) are formed at positions corresponding to the two first feature lines CL1 on the intersection curve CC, respectively. Measurement information is calculated on the basis of the positions of the first spots SP1 positioned on the subject. Further, as shown in FIG. 6, the auxiliary measurement light may include a plurality of second feature lines CL2, which are different from the first feature lines CL1, between the two first feature lines CL1. In a case where the subject is irradiated with the auxiliary measurement light including the first feature lines CL1 and the second feature lines CL2, second spots SP2 (second feature points) are formed at positions corresponding to the plurality of second feature lines CL2, respectively. The second spots SP2 are smaller than the first spots SP1 and an interval between the second spots SP2 is short. For this reason, a specific intersection curve SCC is formed on the intersection curve CC by the plurality of second spots SP2. Measurement information is calculated on the basis of the position of the specific intersection curve SCC.

Figure 7:
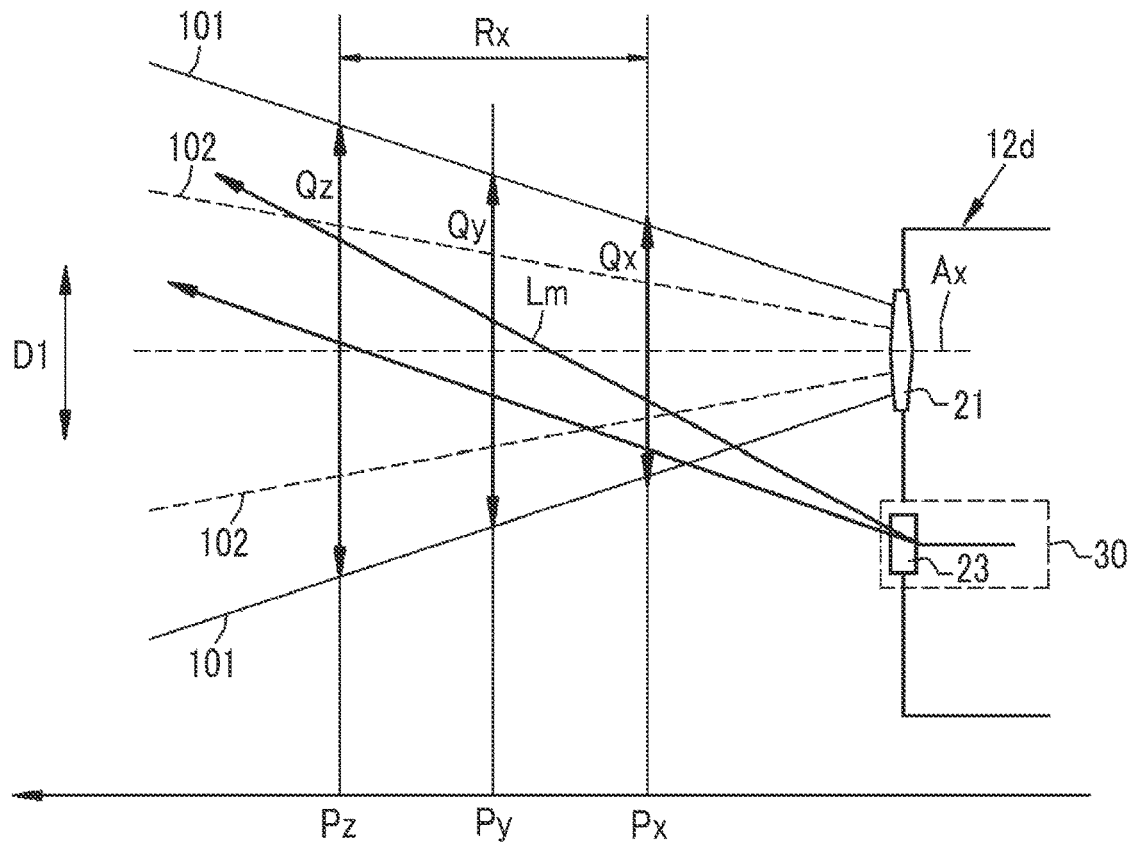
FIG. 7 is a diagram illustrating a relationship between the distal end portion of the endoscope and a near end Px, an intermediate vicinity Py, and a far end Pz in a range Rx of an observation distance.

In regard to the travel direction of the auxiliary measurement light, the auxiliary measurement light is emitted in a state where an optical axis Lm of the auxiliary measurement light crosses the optical axis Ax of the objective lens 21 as shown in FIG. 7. In a case where the subject can be observed in a range Rx of an observation distance, it is understood that the positions (points where the respective arrows Qx, Qy, and Qz cross the optical axis Ax) of the first spots SP1 or the second spots SP2 formed on the subject by the auxiliary measurement light in imaging ranges (shown by arrows Qx, Qy, and Qz) at a near end Px, an intermediate vicinity Py, and a far end Pz of the range Rx are different from each other. The imaging angle of view of the imaging optical system is represented by an area between two solid lines 101, and measurement is performed in a central area (an area between two dotted lines 102), in which an aberration is small, of this imaging angle of view.

Since the auxiliary measurement light is emitted in a state where the optical axis Lm of the auxiliary measurement light crosses the optical axis Ax as described above, sensitivity to the movement of the position of a spot with respect to a change in the observation distance is high. Accordingly, the size of the subject can be measured with high accuracy. Then, the subject illuminated with the auxiliary measurement light is imaged by the imaging element 32, so that the taken image including the first spots SP1 or the second spots SP2 is obtained. In the taken image, the positions of the first spots SP1 or the second spots SP2 depends on a relationship between the optical axis Ax of the objective lens 21 and the optical axis Lm of the auxiliary measurement light and an observation distance. The number of pixels representing the same actual size (for example, 5 mm) is increased in the case of a short observation distance, and the number of pixels representing the same actual size (for example, 5 nm) is reduced in the case of a long observation distance.

Accordingly, in a case where information representing a relationship between the positions of the first spots SP1 or the second spots SP2 and measurement information (the number of pixels) corresponding to the actual size of the subject is stored in advance as described in detail below, measurement information can be calculated from the positions of the first spots SP1 or the second spots SP2.

Figure 8:
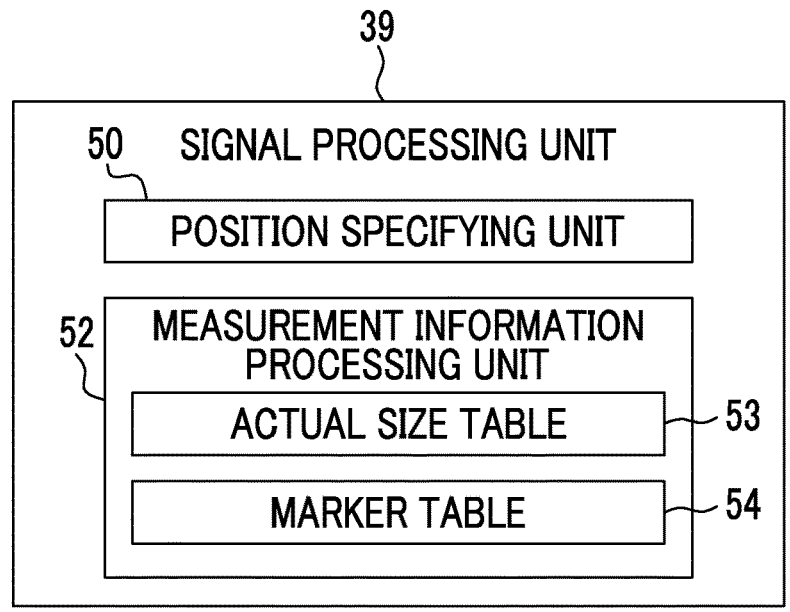
FIG. 8 is a block diagram showing the function of a signal processing unit.

As shown in FIG. 8, the signal processing unit 39 of the processor device 16 includes a position specifying unit 50 and a measurement information processing unit 52 to recognize the positions of the first spots SP1 or the second spots SP2 and to calculate measurement information. In a case where the endoscope 12 is set to the length measurement mode, the taken image including the first spots SP1 or the second spots SP2 is input to the signal processing unit 39. The taken image, which includes the first spots SP1 or the second spots SP2, is acquired by the communication I/F 38 (image acquisition unit).

The position specifying unit 50 specifies the positions of the first spots SP1 or the second spots SP2 from the taken image. The first spots SP1 or the second spots SP2 are displayed in the taken image as substantially circular green areas that include many components corresponding to the color of the auxiliary measurement light. Accordingly, the position specifying unit 50 specifies the positions of the first spots SP1 or the second spots SP2 from the substantially circular green areas. As a method of specifying the positions, for example, there is a method including binarizing the taken image and specifying the centers of white portions (pixels where signal strength is higher than a threshold value for binarization) of the binarized image as the positions of the first spots SP1 or the second spots SP2.

The measurement information processing unit 52 calculates measurement information from the positions of the first spots SP1 or the second spots SP2. The calculated measurement information is displayed in the taken image by the display control unit 40. In a case where the measurement information is calculated on the basis of the positions of the two first spots SP1, measurement information can be accurately calculated even though the subject has a three-dimensional shape. Further, since the positions of the two first spots SP1 are automatically recognized by the processor device 16, a burden is not imposed on a user in acquiring the positions of these two first spots SP1. Furthermore, even though the position of the intersection curve is changed due to the movement of the subject, the two first spots SP1 on the intersection curve are automatically recognized and measurement information is calculated on the basis of the result of the recognition. Accordingly, measurement information can be acquired from the motion picture of the taken image.

Figure 9:
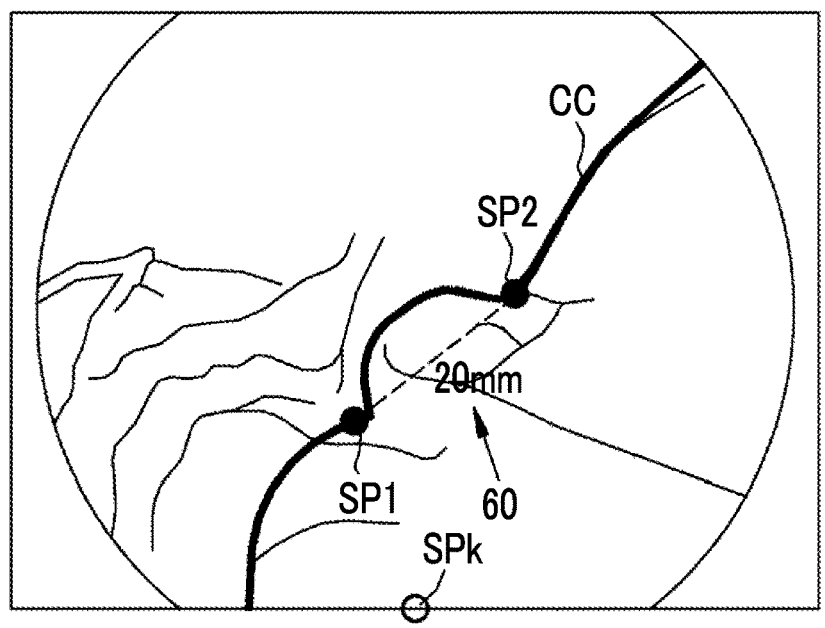
FIG. 9 is a diagram illustrating a first straight-line distance.
Figure 10:
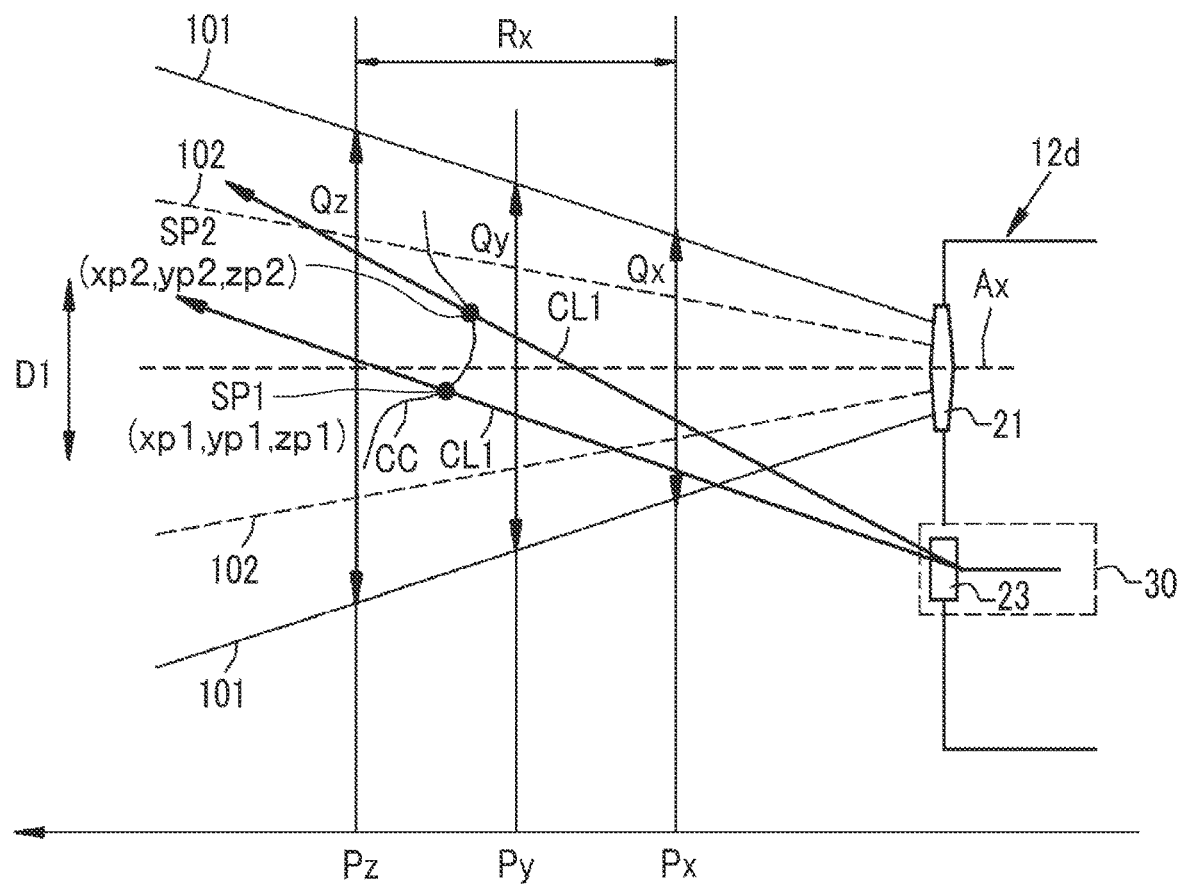
FIG. 10 is a diagram illustrating a method of calculating the first straight-line distance.

As shown in FIG. 9, the measurement information includes a first straight-line distance that represents a straight-line distance between two first and second spots SP1 and SP2. The measurement information processing unit 52 calculates the first straight-line distance by the following method. As shown in FIG. 10, the measurement information processing unit 52 obtains coordinates (xp1, yp1, zp1), which represent the actual size of the subject at the first spot SP1, on the basis of the position of the first spot SP1. Here, coordinates, which are obtained from the coordinates of the position of the first spot SP1 in the taken image and correspond to the actual size, are obtained as xp1 and yp1. A coordinate, which is obtained from the coordinates of the position of the first spot SP1 and the coordinates of the position of a predetermined specific spot SPk (specific point) and corresponds to the actual size, is obtained as zp1. Likewise, the measurement information processing unit 52 obtains coordinates (xp2, yp2, zp2), which represent the actual size of the subject at the second spot SP2, on the basis of the position of the second spots SP2. Further, coordinates, which are obtained from the coordinates of the position of the second spot SP2 in the taken image and correspond to the actual size, are obtained as xp2 and yp2. A coordinate, which is obtained from the coordinates of the position of the second spot SP2 and the coordinates of the position of the predetermined specific spot SPk (specific point) and corresponds to the actual size, is obtained as zp2. Then, the first straight-line distance is calculated by the following equation.

$$\text{First straight-line distance} = ((xp2-xp1)^2+(yp2-yp1)^2+(zp2-zp1)^2)^{0.5} \quad \text{Equation)}$$

The calculated first straight-line distance is displayed in the taken image as measurement information 60 ("20 mm" in FIG. 9). The specific spot SPk may be displayed on the monitor 18, or may not be displayed.

Figure 11:
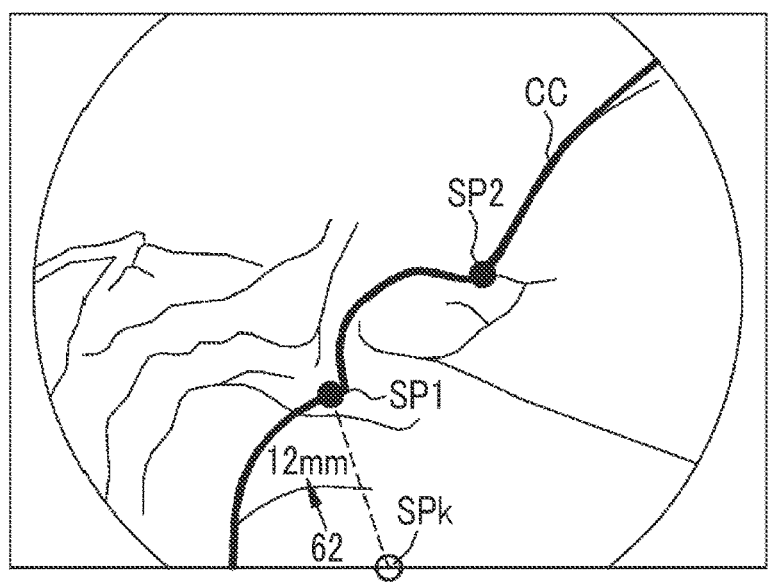
FIG. 11 is a diagram illustrating a second straight-line distance.

Furthermore, as shown in FIG. 11, the measurement information includes a second straight-line distance that represents a straight-line distance between one ("SP1" in FIG. 11) of the two first and second spots SP1 and SP2 and the specific spot SPk (specific point). For example, in a case where the second straight-line distance between the first spot SP1 and the specific spot SPk is to be obtained, the measurement information processing unit 52 obtains the coordinate zp1 that is obtained from the coordinates of the position of the first spot SP1 and the coordinates of the position of the predetermined specific spot SPk (specific point) and corresponds to the actual size. The coordinate zp1 corresponds to the second straight-line distance between the first spots SP1 and the specific spot SPk. The calculated second straight-line distance is displayed in the taken image as measurement information 62 ("12 mm" in FIG. 11).

Figure 12:
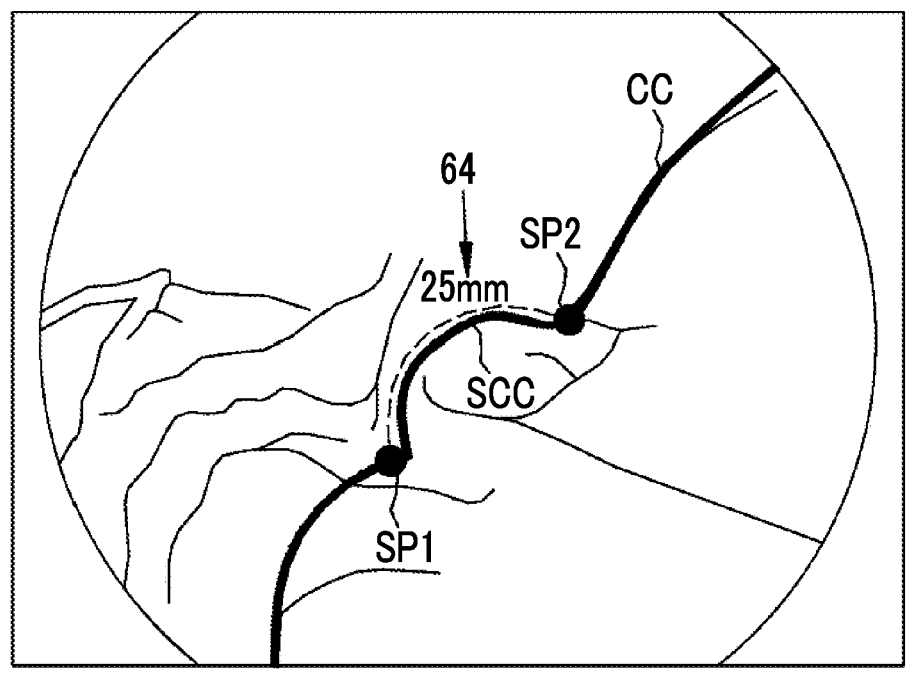
FIG. 12 is a diagram illustrating the length of a specific intersection curve.
Figure 13:
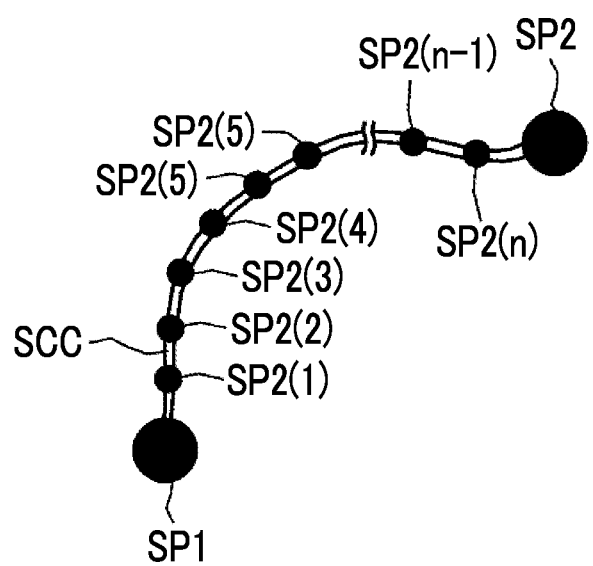
FIG. 13 is a diagram illustrating a method of calculating the length of the specific intersection curve.
Figure 14:
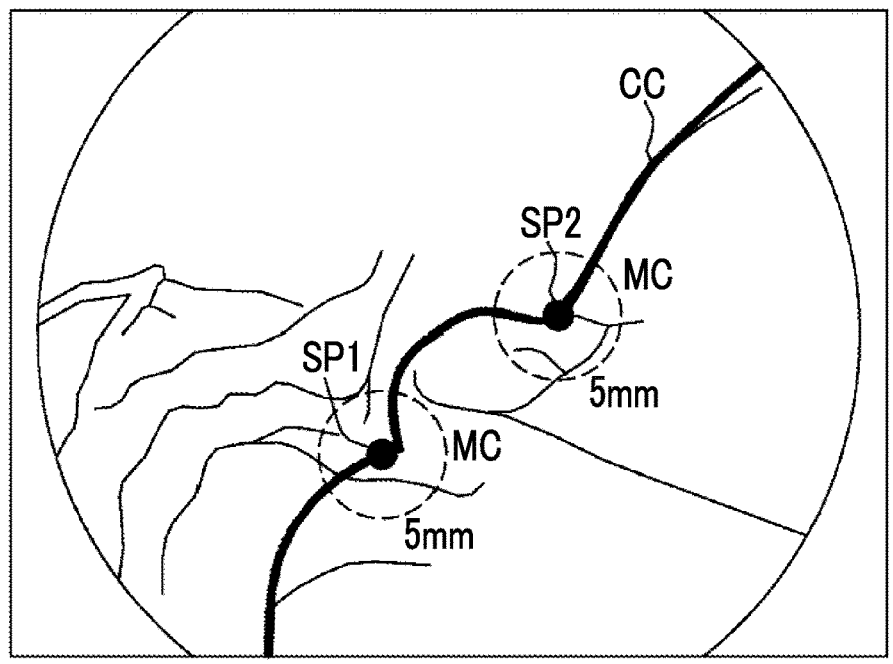
FIG. 14 is a diagram illustrating measurement markers having the shape of a concentric circle.

As shown in FIG. 12, the measurement information includes the length of the specific intersection curve SCC of the intersection curve CC that is positioned between the two first and second spots SP1 and SP2. The measurement information processing unit 52 calculates the length of the specific intersection curve SCC by the following method. As shown in FIG. 13, a first straight-line distance between the first spot SP1 and a second spot SP2(1), which is adjacent to the first spot SP1, on the specific intersection curve SCC is obtained, and the obtained first straight-line distance is denoted by SCC(0). Here, a method of calculating the first straight-line distance is the same as the above-mentioned method (the same applies hereinafter). Then, a first straight-line distance between the second spot SP2(1) and a second spot SP2(2), which is adjacent to the second spot SP2(1), on the specific intersection curve SCC is obtained, and the obtained first straight-line distance is denoted by SL(1).

A first straight-line distance SCC(3) between a second spot SP2(3) and a second spot SP2(4), . . . , a first straight-line distance SL(n-1) between a second spot SP2(n-1) and a second spot SP2(n) (n is a natural number of 2 or more) are calculated by the above-mentioned method. Further, a first straight-line distance SL(n) between a second spot SP(n) and a second spot SP, which is adjacent to the second spot SP(n), is calculated. Then, all the obtained first straight-line distances SL(0), SL(1), . . . , SL(n-1), and SL(n) are added together, so that the length of the specific intersection curve SCC is calculated. The calculated length of the specific intersection curve SCC is displayed in the taken image as measurement information 64 ("25 mm" in FIG. 12).

As shown in 14, the measurement information includes measurement markers representing the actual size of the subject. For example, measurement markers MC, which have centers at the first and second spots SP1 and SP2 and have the shape of a concentric circle, are included as the measurement markers. The measurement markers MC having the shape of a concentric circle represent that distances from the first and second spots SP1 and SP2 are 5 mm. The measurement markers are displayed in the taken image by the display control unit 40. The measurement information processing unit 52 generates the measurement markers on the basis of the positions of the first and second spots SP1 and SP2. Specifically, the measurement information processing unit 52 calculates the sizes of markers from the positions of the spots with reference to a marker table 54 (see FIG. 8) where a relationship between the positions of spots in the taken image and measurement markers representing the actual size of a subject is stored. Then, the measurement information processing unit 52 generates measurement markers corresponding to the sizes of the markers. A method of making the marker table 54 will be described later. A cruciform shape and the like are included as the shape of the measurement marker in addition to the shape of a concentric circle.

The measurement information processing unit 52 calculates at least one of the first straight-line distance, the second straight-line distance, the length of the specific intersection curve, or the measurement markers, as the measurement information. Further, the display control unit 40 may display one or a combination of a plurality of pieces among the measurement information. In this case, the mode changeover switch 13a (measurement information switching unit) is operated to switch the measurement information to be displayed in the taken image to any one of the plurality of pieces of measurement information or a combination of two or more of the plurality of pieces of measurement information. For example, it is preferable that measurement information to be displayed in the taken image is switched in the order of the first straight-line distance→the second straight-line distance→the length of the specific intersection curve→the measurement markers→"a combination of two or more of the first straight-line distance, the second straight-line distance, the length of the specific intersection curve, and the measurement markers" whenever the mode changeover switch 13a is operated. An order in which measurement information is to be switched or types to which measurement information is to be switched can be appropriately changed by the operation of the user interface 19.

Figure 15:
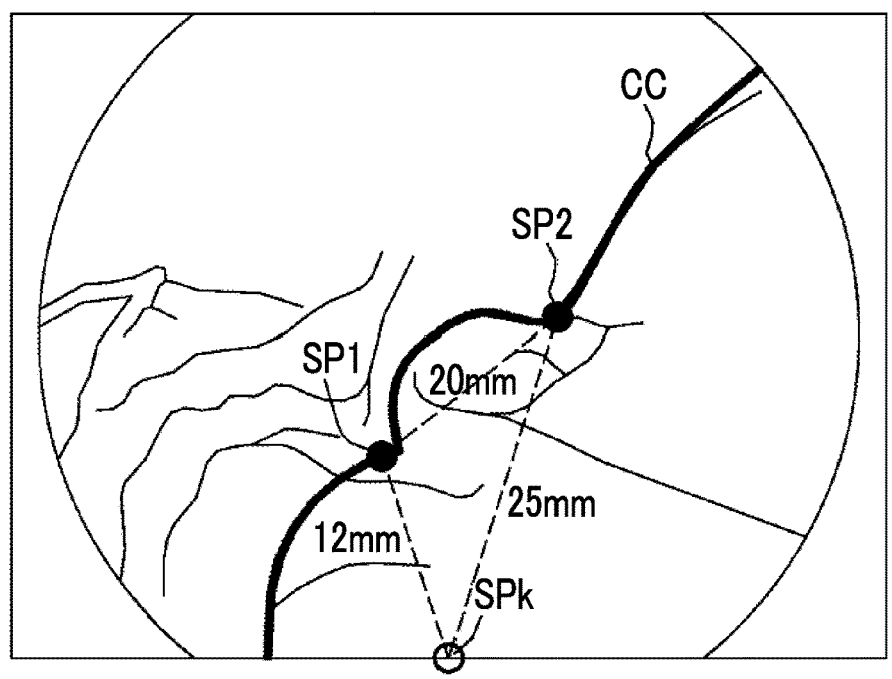
FIG. 15 is a diagram illustrating the first straight-line distance and the second straight-line distance.

In a case where a combination of the first straight-line distance and the second straight-line distance among the plurality of pieces of measurement information is to be displayed, the second straight-line distance between the first spot SP1 and the specific spot SPk ("12 mm" in FIG. 15) and the second straight-line distance between the second spot SP2 and the specific spot SPk ("25 mm" in FIG. 15) are displayed in the taken image in addition to the first straight-line distance between the first spot SP1 and the second spot SP2 ("20 mm" in FIG. 15) as shown in FIG. 15.

Figure 16:
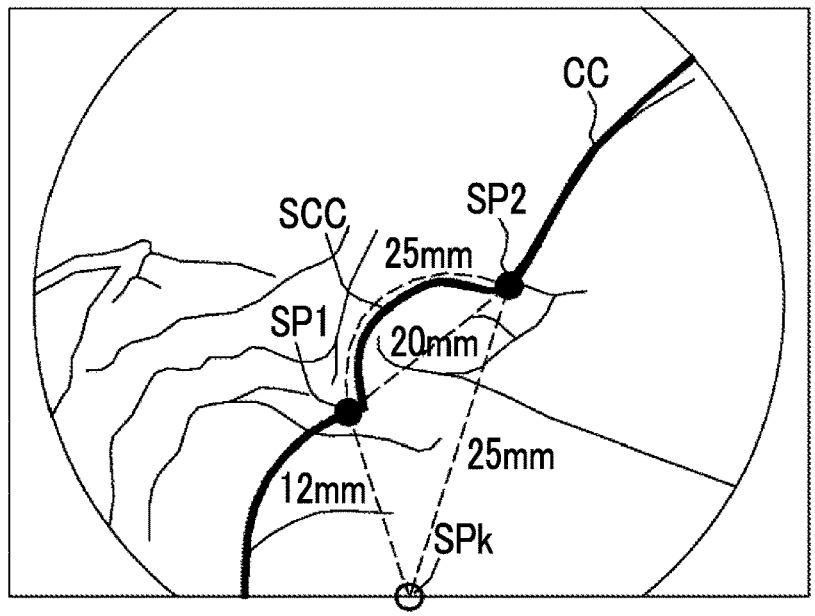
FIG. 16 is a diagram illustrating the lengths of the first straight-line distance, the second straight-line distance, and the specific intersection curve.

Further, in a case where a combination of the first straight-line distance, the second straight-line distance, and the length of the specific intersection curve among the plurality of pieces of measurement information is to be displayed, the second straight-line distance between the first spot SP1 and the specific spot SPk ("12 mm" in FIG. 16), the second straight-line distance between the second spot SP2 and the specific spot SPk ("25 mm" in FIG. 16), and the length of the specific intersection curve ("25 mm" in FIG. 16) are displayed in the taken image in addition to the first straight-line distance between the first spot SP1 and the second spot SP2 ("20 mm" in FIG. 16) as shown in FIG. 16.

A method of making the marker table 54 will be described below. A relationship between the position of a spot and the size of a marker can be obtained through the imaging of a chart where a pattern having the actual size is regularly formed. For example, auxiliary measurement light is emitted to the chart; a graph paper-shaped chart including lines (5 mm) having the same size as the actual size or lines (for example, 1 mm) having a size smaller than the actual size is imaged while an observation distance is changed to change the position of a spot; and a relationship between the position of a spot (pixel coordinates of the spot on the imaging surface of the imaging element 32) and the number of pixels corresponding to the actual size (pixels showing 5 mm that is the actual size) is acquired.

Figure 17:
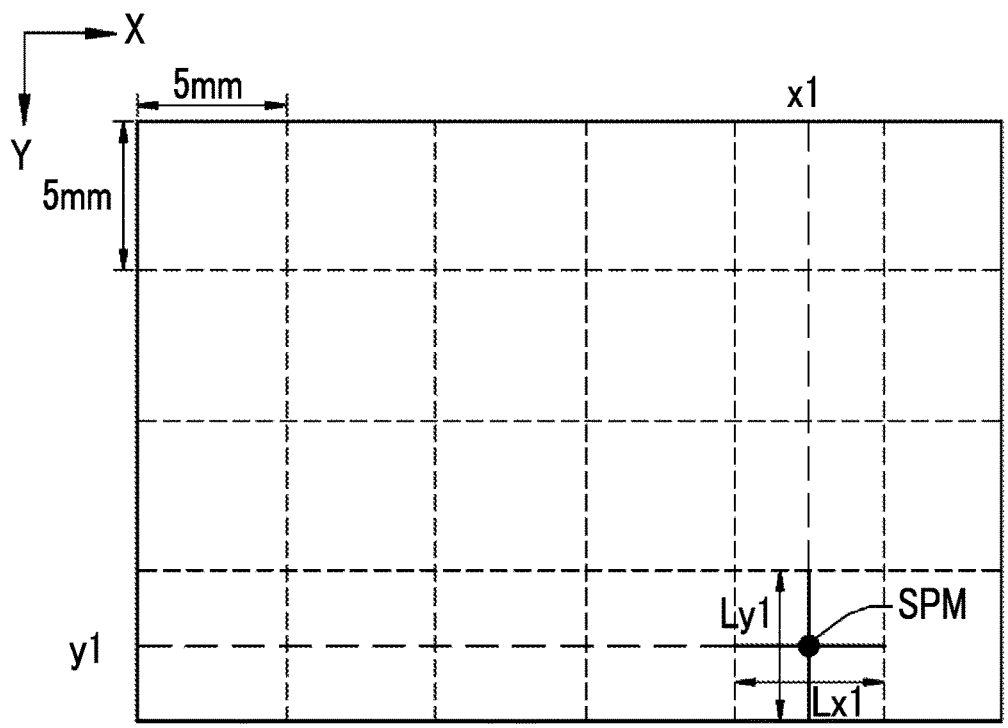
FIG. 17 is a diagram illustrating a graph paper-shaped chart that is used to measure a relationship between the position of a spot and the size of a second measurement marker in a case where an observation distance corresponds to the near end Px.
Figure 18:
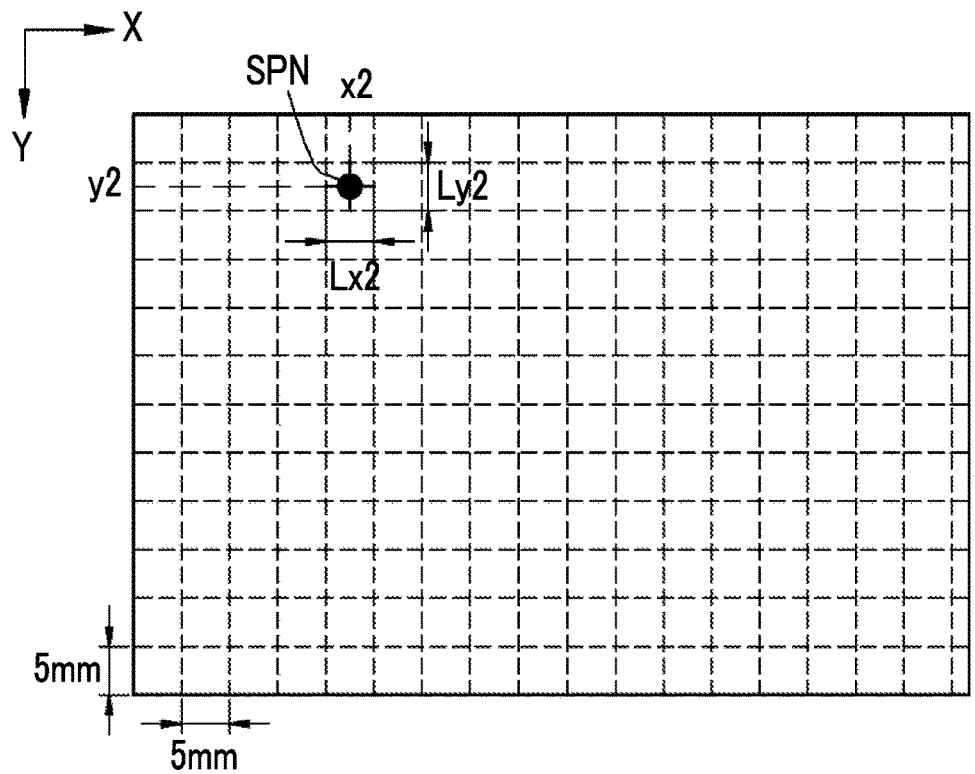
FIG. 18 is a diagram illustrating a graph paper-shaped chart that is used to measure a relationship between the position of a spot and the size of the second measurement marker in a case where an observation distance corresponds to the far end Pz.

As shown in FIG. 17, (x1, y1) means the pixel position of a spot SPM in an X direction and a Y direction on the imaging surface of the imaging element 32 (an upper left point is the origin of a coordinate system). The number of pixels in the X direction, which corresponds to the actual size of 5 mm, at the position (x1, y1) of the spot SPM is denoted by Lx1, and the number of pixels in the Y direction is denoted by Ly1. This measurement is repeated while an observation distance is changed. FIG. 18 shows a state where the chart including lines having a size of 5 mm as in FIG. 17 is imaged, but an interval between the lines is narrow since this state is a state where an observation distance is closer to the far end than that in the state of FIG. 17. In the state of FIG. 18, the number of pixels in the X direction, which corresponds to the actual size of 5 mm, at the position (x2, y2) of a spot SPN on the imaging surface of the imaging element 32 is denoted by Lx2, and the number of pixels in the Y direction is denoted by Ly2. Then, while an observation distance is changed, the same measurement as those in FIGS. 17 and 18 is repeated and the results thereof are plotted. The charts are shown in FIGS. 17 and 18 without consideration for the distortion of the objective lens 21.

Figure 19:
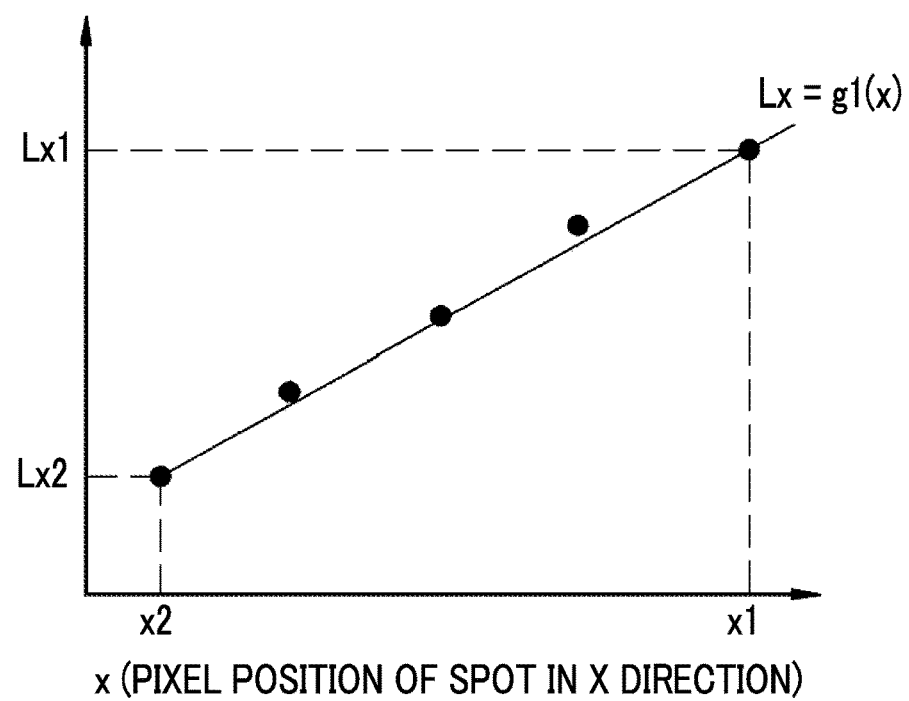
FIG. 19 is a graph showing a relationship between the pixel position of a spot in an X direction and the number of pixels of the second measurement marker in the X direction.
Figure 20:
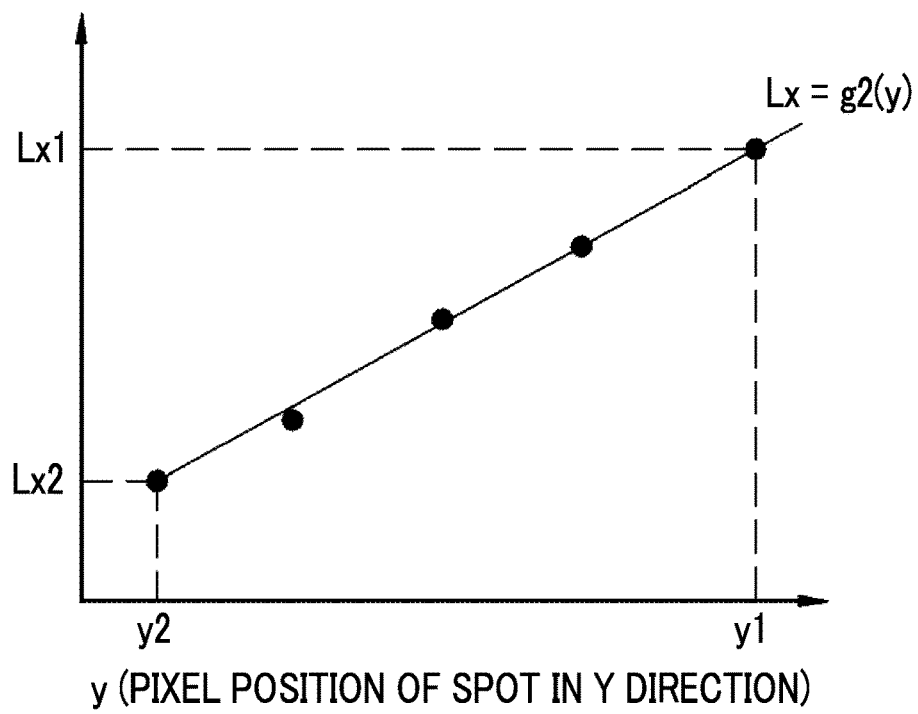
FIG. 20 is a graph showing a relationship between the pixel position of a spot in a Y direction and the number of pixels of the second measurement marker in the X direction.

FIG. 19 shows a relationship between the X-coordinate of the position of a spot and Lx (the number of pixels of a second measurement marker in the X direction), and FIG. 20 shows a relationship between the Y-coordinate of the position of a spot and Lx. Lx is expressed by "Lx=g1(x)" as a function of the position in the X direction from the relationship of FIG. 19, and Lx is expressed by "Lx=g2(y)" as a function of the position in the Y direction from the relationship of FIG. 20. The functions g1 and g2 can be obtained from the above-mentioned plotted results by, for example, a least-square method.

The X-coordinate of a spot corresponds to the Y-coordinate of a spot one to one, and basically the same results are obtained (the same number of pixels is obtained at the position of the same spot) even though any one of the function g1 or g2 is used. Accordingly, in a case where the size of the second measurement marker is to be calculated, any one of the function g1 or g2 may be used and a function of which sensitivity to a change in the number of pixels with respect to a change in position is higher may be selected from the functions g1 and g2. Further, in a case where the values of the functions g1 and g2 are significantly different from each other, it may be determined that "the position of a spot cannot be recognized".

Figure 21:
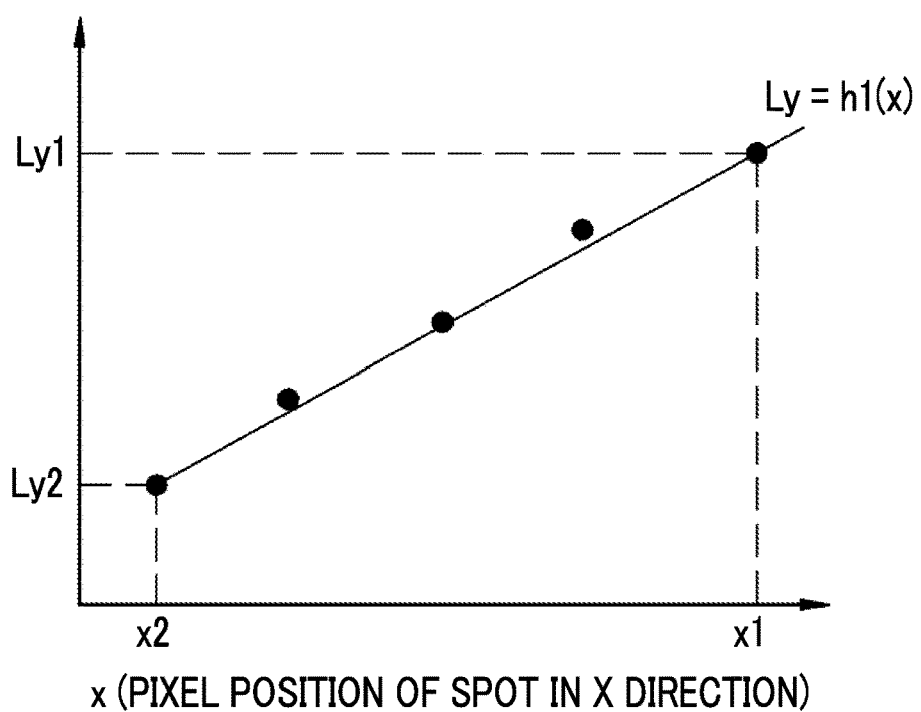
FIG. 21 is a graph showing a relationship between the pixel position of a spot in the X direction and the number of pixels of the second measurement marker in the Y direction.
Figure 22:
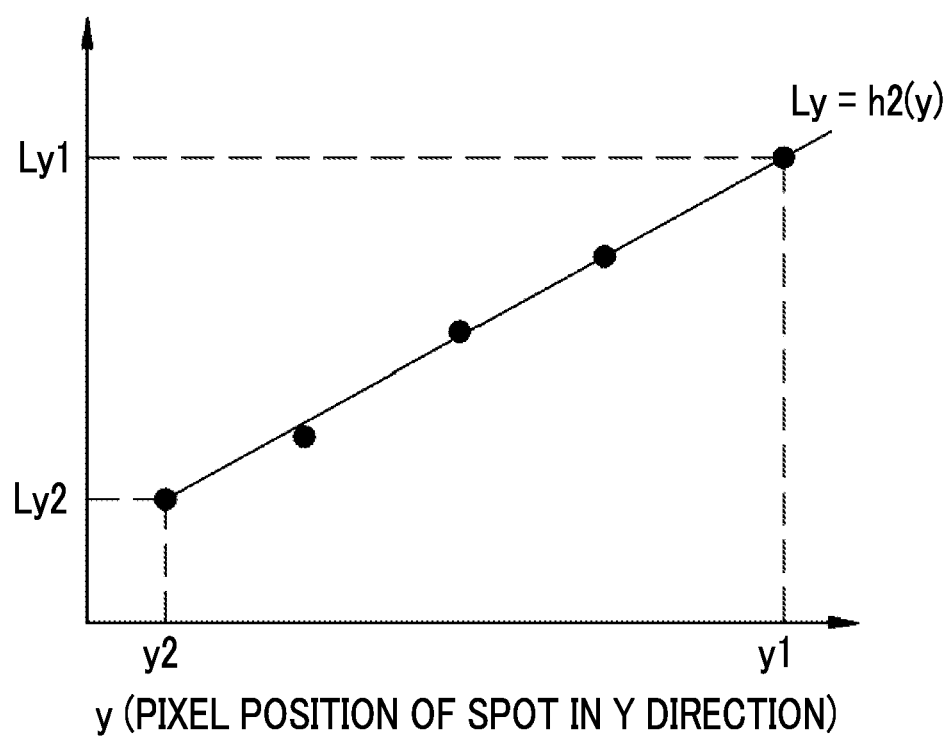
FIG. 22 is a graph showing a relationship between the pixel position of a spot in the Y direction and the number of pixels of the second measurement marker in the Y direction.

FIG. 21 shows a relationship between the X-coordinate of the position of a spot and Ly (the number of pixels in the Y direction), and FIG. 22 shows a relationship between the Y-coordinate of the position of a spot and Ly. Ly is expressed by "Ly=h1(x)" as the coordinate of the position in the X direction from the relationship of FIG. 21, and Ly is expressed by "Ly=h2(y)" as the coordinate of the position in the Y direction from the relationship of FIG. 22. Any one of the function h1 or h2 may also be used as Ly as in the case of Lx.

The functions g1, g2, h1, and h2 obtained as described above are stored in the marker table in the form of a look-up table. The functions g1 and g2 may be stored in the marker table in the form of a function.

In the embodiment, the hardware structures of processing units, which perform various kinds of processing, such as the signal processing unit 39, the display control unit 40, the system control unit 41, the position specifying unit 50, and the measurement information processing unit 52, are various processors to be described later. Various processors include: a central processing unit (CPU) that is a general-purpose processor functioning as various processing units by executing software (program); a programmable logic device (PLD) that is a processor of which the circuit configuration can be changed after the manufacture of a field programmable gate array (FPGA) and the like; a dedicated electrical circuit that is a processor having circuit configuration designed for exclusive use to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software so as to be typified by a computer, such as a client or a server, and functions as a plurality of processing units. Second, there is an aspect where a processor fulfilling the functions of the entire system, which includes a plurality of processing units, by one integrated circuit (IC) chip is used so as to be typified by System On Chip (SoC) or the like. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope apparatus
12: endoscope
12*a*: insertion part
12*b*: operation part
12*c*: bendable portion
12*d*: distal end portion
12*e*: angle knob
13*a*: mode changeover switch
13*b*: freeze switch
14: light source device
16: processor device
18: monitor
19: user interface
21: objective lens
22: illumination lens
23: auxiliary measurement lens
24: opening
25: air/water supply nozzle
26: light source unit
27: light source control unit
28: light guide
29*a*: illumination optical system
29*b*: imaging optical system
30: auxiliary measurement light-emitting unit
30*a*: light source
30*c*: prism
32: imaging element
33: imaging control unit
34: CDS/AGC circuit
35: A/D circuit
36: communication interface (I/F)
37: static image storage unit
38: communication interface (I/F)
39: signal processing unit
40: display control unit
41: system control unit
50: position specifying unit
52: measurement information processing unit
53: actual size table
54: marker table
SP1: first spot
SP2: second spot
SPk: specific spot
CC: intersection curve
SCC: specific intersection curve
MC: measurement marker

What is claimed is:

1. An endoscope apparatus comprising:
an auxiliary measurement light-emitting unit that emits auxiliary measurement light as planar light including at least two first feature lines and a plurality of second feature lines different from the first feature lines, wherein the second feature lines extend between the first feature lines and have a same radial center as the first feature lines;
an imaging sensor that images a subject illuminated with the auxiliary measurement light; and
a processor configured to:
acquire a taken image obtained in a case where the subject is imaged by the imaging sensor, the taken image including an intersection curve formed on the subject and at least two first feature points formed at positions corresponding to the first feature lines on the intersection curve;
specify at least positions of the first feature points on the basis of the taken image;
recognize the positions of the first feature points;
calculate measurement information from the recognized positions of the first feature points; and
display the measurement information representing an actual size of the subject in the taken image by using the positions of the first feature points,
wherein the auxiliary measurement light-emitting unit comprises a light source, a diffractive optical element, and a prism disposed between the light source and the diffractive optical element.

2. The endoscope apparatus according to claim 1, wherein the measurement information includes a first straight-line distance between the two first feature points.

3. The endoscope apparatus according to claim 1,
wherein the measurement information includes a second straight-line distance between one of the two first feature points and a specific point other than the two first feature points.

4. The endoscope apparatus according to claim 1,
wherein the measurement information includes a length of a specific intersection curved portion of the intersection curve positioned between the two first feature points,
the processor specifies a position of the specific intersection curved portion, and
the processor displays the length of the specific intersection curved portion in the taken image by using the positions of the first feature points and the position of the specific intersection curved portion.

5. The endoscope apparatus according to claim 4,
wherein the specific intersection curved portion includes a plurality of second feature points that are formed on the intersection curve by the second feature lines so as to be smaller than the first feature points, and
the processor specifies the position of the specific intersection curved portion from the plurality of second feature points included in the taken image.

6. The endoscope apparatus according to claim 1, further comprising:
a measurement information switch that switches the measurement information to be displayed in the taken image to any one of a plurality of pieces of measurement information or a combination of two or more of a plurality of pieces of measurement information in a case where there are a plurality of pieces of measurement information.

7. The endoscope apparatus according to claim 1, further comprising:
a static image-acquisition command switch that gives a static image-acquisition command to acquire a static image of the taken image,
wherein the measurement information is also stored together in a case where the static image-acquisition command is given.

8. The endoscope apparatus according to claim 1, further comprising:
another light source that emits illumination light for illuminating the subject,
wherein the light source is provided independently of the another light source, and the diffractive optical element is used to obtain the auxiliary measurement light from light emitted from the light source.

9. The endoscope apparatus according to claim 8,
wherein the prism is used to emit the auxiliary measurement light toward the subject in a state where an optical axis of the imaging sensor and an optical axis of the auxiliary measurement light cross each other.

10. The endoscope apparatus according to claim 9,
wherein the prism is provided with an anti-reflection portion.

11. The endoscope apparatus according to claim 8,
wherein the auxiliary measurement light-emitting unit includes an auxiliary measurement slit that is used to emit the auxiliary measurement light toward the subject in a state where an optical axis of the imaging sensor and an optical axis of the auxiliary measurement light cross each other.

12. The endoscope apparatus according to claim 8,
wherein the light source is a laser light source.

13. The endoscope apparatus according to claim 12,
wherein a wavelength of light emitted from the light source is in the range of 495 nm to 570 nm.

* * * * *